(12) United States Patent
Roberts et al.

(10) Patent No.: US 6,267,744 B1
(45) Date of Patent: Jul. 31, 2001

(54) BANDAGES

(75) Inventors: Joanne Carol Roberts, Nelson; John Blackburn, Morecambe, both of (GB)

(73) Assignee: Smith & Nephew Plc, London (GB)

( * ) Notice: Subject to any disclaimer, the term of this patent is extended or adjusted under 35 U.S.C. 154(b) by 0 days.

(21) Appl. No.: 09/446,088

(22) PCT Filed: Jun. 18, 1998

(86) PCT No.: PCT/GB98/01793

§ 371 Date: Apr. 7, 2000

§ 102(e) Date: Apr. 7, 2000

(87) PCT Pub. No.: WO98/58106

PCT Pub. Date: Dec. 23, 1998

(30) Foreign Application Priority Data

Jun. 18, 1997 (GB) .................................................. 9712696

(51) Int. Cl.[7] .................................................. A61F 13/00
(52) U.S. Cl. .................................. 602/76; 602/44; 602/75
(58) Field of Search .................................. 602/41, 44, 60, 602/74–76

(56) References Cited

U.S. PATENT DOCUMENTS

| | | | |
|---|---|---|---|
| 3,921,382 | * 11/1975 | Tsujita et al. | 57/6 |
| 3,940,917 | * 3/1976 | Strachan | 57/152 |
| 4,563,384 | * 1/1986 | Wiehe et al. | 442/153 |
| 6,142,968 | * 11/2000 | Pigg et al. | 602/75 |

FOREIGN PATENT DOCUMENTS

9858106 * 12/1998 (WO) .

* cited by examiner

Primary Examiner—Kim M. Lewis
(74) Attorney, Agent, or Firm—Larson & Taylor PLC

(57) ABSTRACT

A woven fabric comprising warp and weft yarns is characterized in that the warp yarns comprise a plurality of elasticized yarns and twisted inelastic yarns arranged such that the inelastic yarns are in pairs of like twist, with two elastic yarns between. Alternate pairs of inelastic yarn are of opposing direction of twist. Such fabrics may be used for medical bandages such as elasticized adhesive or non-adhesive bandages and support or compression garments such as stockings.

11 Claims, 2 Drawing Sheets

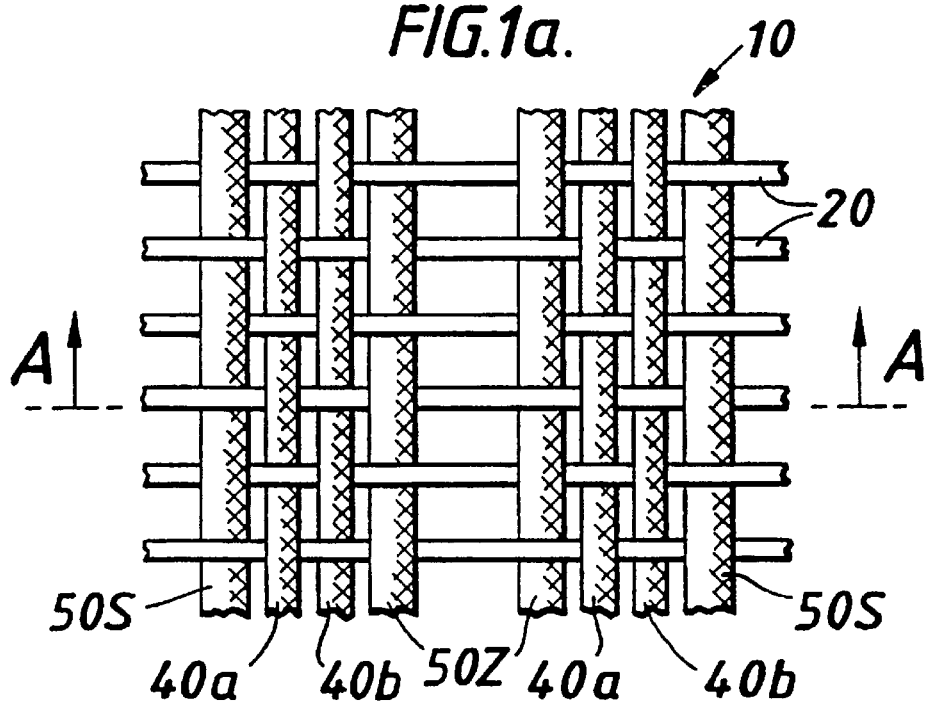
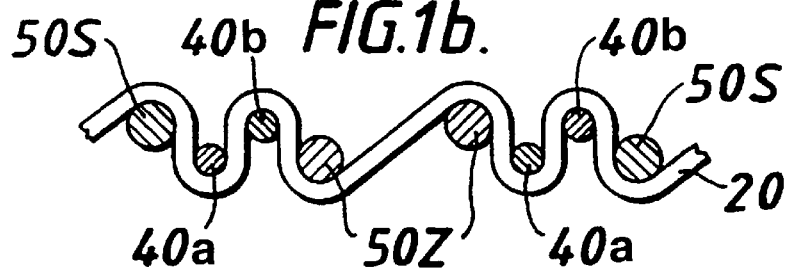
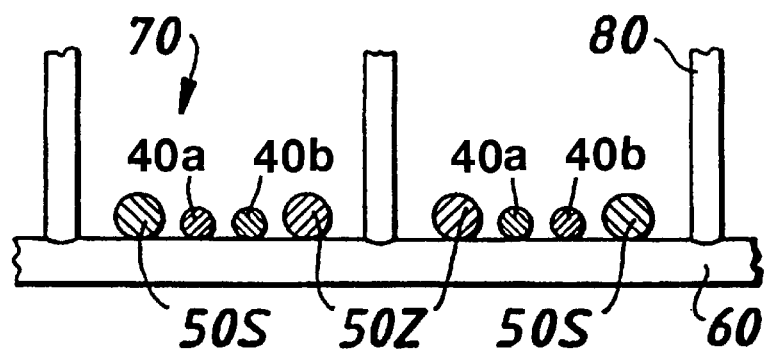

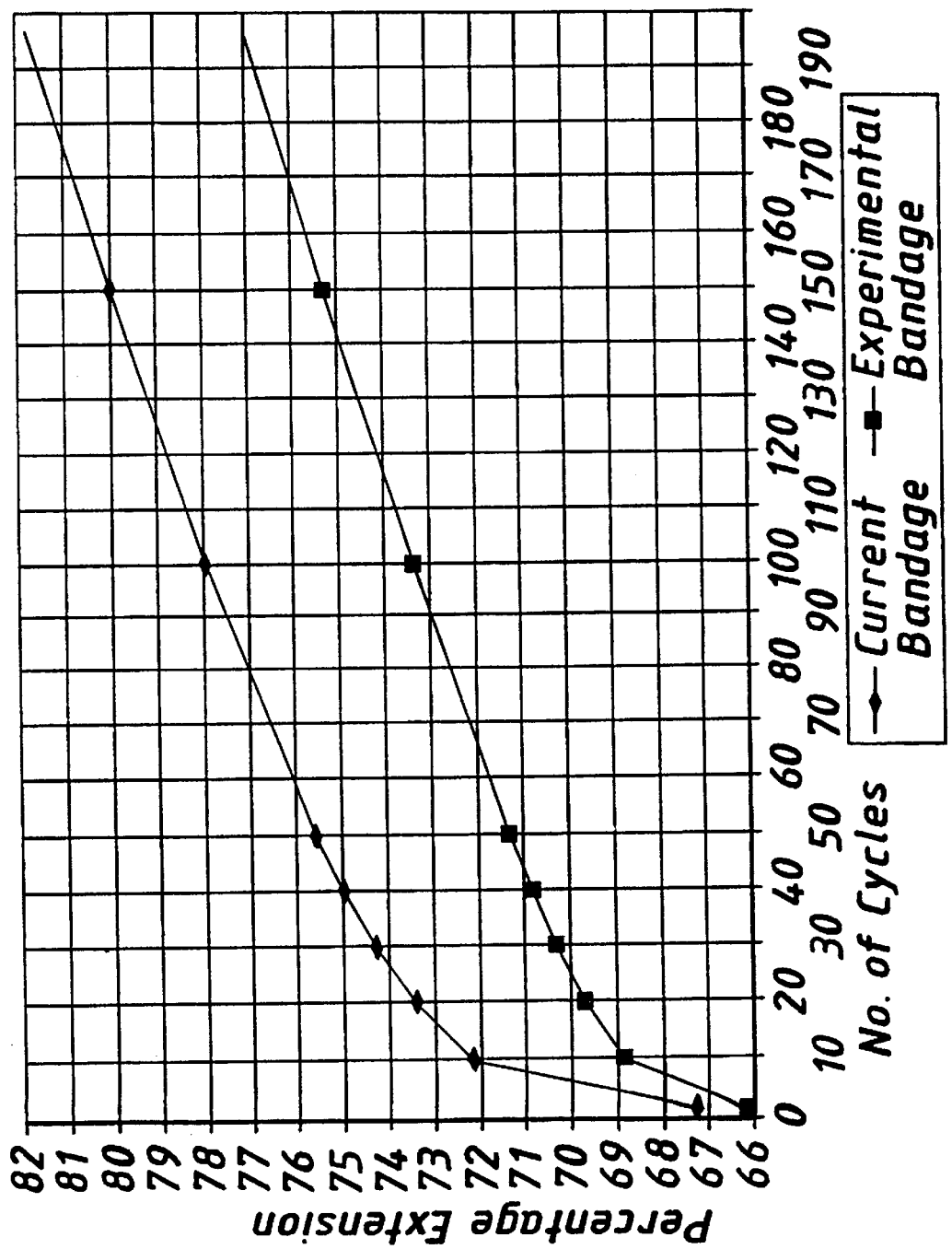
FIG. 2. A Comparison Of The Current EAB & The Experimental EAB-Load Cycling Analysis

BANDAGES

The present invention relates to elasticised materials and more particularly elasticised medical fabrics including adhesive bandaging material and traditional flat crepe non adhesive bandage material which provide strong support. The present invention also relates to processes for the manufacture of such materials.

Elastic adhesive bandages [EAB's] and Elastic bandages [EB's] are normally used to provide support for the treatment of sprains, strains, sports injuries, varicose veins and ulcers.

These bandages are required to have sufficient elasticity to enable them to conform to the body portion contour when applied to bandaged area and, when secured, to allow limited movement. EABs carry a layer of an adhesive such as a pressure sensitive adhesive, to permit the bandage to be fixed in place.

However a problem with conventional EAB's and EB's is that the fabrics stretch but do not recover well thus resulting in fatigue or loss of support during use. A proposed solution has been the inclusion of a percentage of elastomeric yarns in the fabric structure to aid recovery.

Bandages which use elastic and twisted inelastic yarns are know from CH-A637537 and DE-A-2706787.

The present invention seeks to overcome these disadvantages whilst also retaining the conventional EAB aesthetics ie 'herringbone appearance' by the employment of twisted inelastic yarns.

According to the present invention there is a woven fabric comprising warp and weft yarns characterised in that the warp yarns comprise a plurality of elasticised yarns and twisted inelastic yarns arranged such that the inelastic yarns are in pairs of like twist, with two elastic yarns between. Alternate pairs of inelastic yarn are of opposing direction of twist wherein the cross-sectional area of the inelastic yarn is greater than that of the elastic yarn.

According to one embodiment of the present invention there is provided an elastic bandaging material comprising a woven fabric comprising warp and weft yarns characterised in that the warp yarns are elastic yarns and inelastic yarns arranged such that on each side of the elastic yarn is an inelastic yarn, each inelastic yarn with an opposing twist, so that adjacent inelastic yarns are always of the same direction.

According to a second aspect of the present invention there is provided an elastic adhesive bandaging material comprising a woven fabric having a layer of an adhesive on one side thereof wherein the fabric comprises warp and weft yarns characterised in that the warp yarns comprise a plurality of elasticised yarns and twisted inelastic yarns arranged such that the inelastic yarns are in pairs of like twist, with two elastic yarns between. Alternate pairs of inelastic yarn are of opposing direction of twist.

According to a further embodiment of the second aspect of the present invention there is provided an elastic adhesive bandaging material comprising a woven fabric with a backside and a face side with an adhesive applied to the back side wherein the fabric comprises warp and weft yarns characterised in that the warp yarns are elastic yarns and inelastic yarns arranged such that on each side of the elastic yarns is an inelastic yarn, each inelastic yarn with an opposing twist, so that adjacent inelastic yarns are always of the same direction of twist.

Aptly the twisted inelastic yarns will have much larger cross-sectional area than the elasticised yarns. This will have the effect of burying the elasticised yarn within the fabric, by rolling of the twisted inelastic yarn over the elasticised yarn. The size of the cross-sectional area or thickness of the twisted yarn will be determined not only by the diameter of the filaments comprising the yarn but also by virtue of the bulking induced by the twisting of the yarn. Aptly, the thickness of the elasticised yarn will range from 40 to about 80 Decitex whereas in the case of cotton inelastic yarns the Cotton Count will aptly range from 48 to 12 and will most aptly be about 28.

The inelastic yarns will be imparted with a twist, suitably a light twist and will preferably have twist of from 4 to 16 turns/cm (10 to 40 turns per inch), more suitably about 8 turns/cm (20 turns per inch). The inelastic yarns are provided with either an S-twist or a Z-twist and these yarns will be aligned in the warp direction in the fabric such that immediately neighbouring inelastic yarns have the same twists. Suitable materials for use as the inelastic yarn may comprise natural materials such as cellulosic fibres, for example cotton, synthetic materials such as viscose or mixed fibres As used herein the term the "elasticised" refers to fabric components which are capable of being extended on the application of a stretching force and, upon release of that force will revert to or nearly to their original length. Such materials are elastic by virtue of the properties of the materials forming the structure or by virtue of the physical construction of the component The elasticised yarns for use in the present invention aptly have an elastically recoverable extension of from 50 to 120%, more suitably from 65 to 75% and typically about 69%.

One type of suitable yarn for use as the elasticised yarn may be that formed from crimped or twisted inelastic materials such as heat-set crimped Nylon or very highly twisted cotton fibres (for example having a Twist Factor of greater than 16). Such materials although not truly elastic in nature can be stretched and upon relaxation of the stretching force will return to their crimped or highly twisted state.

Another and preferred type of elasticised yarns are those formed from elastomers such as polyurethane, natural rubber or synthetic rubbers such as neoprene and chloroprene. Such elastomer based yarns may be mono- or multi-filamentary in nature and may be wrapped with an inelastic yarn to limit the extensibilty of the elastomeric component of the prior to lock-out. A preferred elasticised yarn is a nylon wrapped polyurethane yarn sold by DuPont under the trade mark LYCRA. Such wrapped yarns may be singly or doubly wrapped. A suitable wrapped yarn for the purpose of this invention is a single wrapped yarn wrapped with from 680 to 750 turns per meter of a synthetic or natural fibre yarn. Typically such wrapped yarns have about 715 turns of wrapping yarn.

The desired ratio and relationship both among and between the elasticised and inelastic yarns can selected and maintained by the adoption of an appropriate denting arrangement in the front reed of the loom from which the fabric is woven.

The elasticised and inelastic yarns may be arranged such that that each twisted inelastic yarn lies immediately adjacent an elasticised yarn and such that the inelastic yarns in the same dent have opposing twists. One suitable arrangement of yarns in dent consists of four yarns, two inelastic and two elasticised yarns in which the two elasticised yarns lie immediately adjacent to each other and each has an associated twisted inelastic yarn. The inelastic yarns have S- and Z-twists respectively. In an alternative arrangement the dent arrangement consists of three yarns, a single elasticised yarn and two inelastic yarns, having S- and Z-twists respectively. In each instance each inelastic yarn is paired with an inelastic yarn, in the adjacent dent, having a like twist.

The weft yarns for use in the fabrics of the present invention may comprise yarns conventionally used for the weft of elasticised fabrics such as EABs and EBs. One such material suitable for use in the invention is cotton.

The fabrics of the invention are elastic in nature and may be used in those conventional garment and bandaging applications requiring the use of elasticised fabrics.

Thus in accordance with the invention there is provided a medical bandage comprising a woven fabric having warp and weft yarns characterised in that the warp yarns comprise a plurality of elasticised yarns and twisted inelastic yarns arranged such that the inelastic yarns are in pairs of like twist, with at least one elasticised yarn therebetween and in that alternate pairs of inelastic yarns have opposing directions of twist.

In accordance with a further aspect of the invention there is provided a compression or support garment comprising a woven fabric having warp and weft yarns characterised in that the warp yarns comprise a plurality of elasticised yarns and twisted inelastic yarns arranged such that the inelastic yarns are in pairs of like twist, with at least one elasticised yarn therebetween and in that alternate pairs of inelastic yarn have opposing directions of twist. Preferably there are two elasticised yarns between each pair of inelastic yarns of like twist. Examples of support garment manufactured from the fabrics of the invention include support hosiery and body stockings.

The invention will now be described by example with reference to the accompanying figures.

FIG. 1a shows the make up of the woven fabric where a single pick 20 is shown in a schematic plan view. In some cases of narrow weaving with needle looms two picks will be inserted.

FIG. 1b illustrates a schematic cross-section of the fabric in the line A—A shown in FIG. 1a FIG. 2 shows experimental results from testing fatigue properties of an EAB comprising a fabric shown in FIG. 1 coated on one side with an adhesive.

FIG. 3 shows a typical denting arrangement of yarns for weaving fabrics of the present invention.

Referring to FIGS. 1a and 1b, the weft yarns 20 of a woven fabric 10 are typically cotton yarns and the warp yarns comprise an arrangement whereby two elastic yarns 40a, 40b are flanked respectively on each side by cotton yarns 50Z, 50S so that adjacent inelastic yarns are of the same twist. Each flanking cotton yarn has 20 turns per inch. Yarn 50Z has a Z-twist and yarn 50S an S-twist.

FIG. 3 shows a reed 60 which is a closed comb of flat metal strips or reed wires 80 which are uniformly spaced at intervals corresponding to the required spacing of the warp ends. The spaces between the metal strips through which the ends pass are known as dents 70. The warp arrangement through the reed to produce a fabric as illustrated in FIG. 1a is such that four ends pass through the dent. These four ends consist of one cotton of S twist (50S) and one cotton Z twist (50S) either side of two elastic ends 40a, 40b. A front reed is used in the weaving process to hold the warp threads at uniform spacings and to beat up the newly inserted picks of weft. The dents push the outer inelastic twist yarns towards the centre as the weaving occurs and this aids the rolling of the inelastic yarn over the elastic yarn.

EXAMPLE

A commercially available EAB was produced according to the specification for BP Cotton Crepe (as defined in the British Pharmacoepia) and subjected to a cyclic stretching and relaxation test (known as Load Cycling).

An EAB of the present invention was subjected to the same Load Cycling test. The EAB of the invention consisted of a weft of twisted (11 turns per inch/about 4 turns per centimeter) cotton yarns having a Cotton Count of 8 and a warp of elasticised and inelastic yarns, having the denting arrangement shown in FIGS. 1a and 1b. The elasticised yarn was wrapped polyurethane yarn in which the polyurethane component was 78 Decitex yarn and the wrapping yarn was 78 Decitex nylon. The inelastic yarns comprised comprised cotton two-fold 28s resultant 14s yarns having S- or Z-twists (20 turns inch$^{-1}$/about 8 turns cm$^{-1}$)

As the test progresses the bandages suffer fatigue and exhibit progressively less and less elastic recovery ie the bandages get longer and longer when in their relaxed condition.

The following table details the percentage extension at the given cycle intervals for bandages of the present invention compared with prior art bandages. FIG. 2 shows the same results but represented graphically.

| | Percentage Extension | |
|---|---|---|
| Cycle No. | Commercial EAB | EAB of the present invention. |
| 1 | 67.22 | 66.08 |
| 10 | 72.12 | 68.84 |
| 20 | 73.41 | 69.68 |
| 30 | 74.26 | 70.30 |
| 40 | 74.96 | 70.82 |
| 50 | 75.56 | 71.31 |
| 100 | 77.97 | 73.40 |
| 150 | 80.02 | 75.27 |
| 200 | 81.90 | 77.09 |

The results show that the EAB of the present invention fatigue less quickly than the commercial EAB.

Similarly, FIG. 2 shows that during the period of cycling both bandages increased in length. Initially the bandages start at almost the same point, but by the end of the test the commercial EAB had extended almost 5% more than the EAB of the present invention.

After only 10 cycles the commercial EAB has extended 3% more than the EAB of the present invention.

By using gradients and indices an overall rate of fatigue has been calculated for the bandages so that bandages may be ranked in order of which fatigues faster/slower. The commercial EAB has a index value of 230 whereas the EAB of the present invention has an index value of 138, the lower the number the slower the fatigue rate.

What is claimed is:

1. A woven fabric (10) comprising warp (50S, 40a, 40b, 50Z) and weft yarns (20) characterised in that the warp yarns (50S, 40a, 40b, 50Z) comprise a plurality of elasticised yarns (40a, 40b) and twisted inelastic yarns (50S, 50Z) arranged such that the inelastic yarns are in pair of like twist (50S or 50Z, with at least two elasticised yarns (40a, 40b) therebetween, wherein alternate pairs of inelastic yarn (50S, 50Z) have of opposing directions of twist, and wherein the cross-sectional area of the inelastic yarn (50S, 50Z) is greater than that of the elastic yarn (40a, 40b).

2. The fabric (10) as claimed in claim 1 wherein, the thickness of the elasticised yarn (40a, 40b) is from 40 to 80 Decitex.

3. The fabric (10) as claimed in claim 1 wherein the inelastic yarn (50S, 50Z) is a cotton yarn.

4. The fabric (10) as claimed in claim 3 wherein the yarn has a Cotton Count of from 48 to 12.

5. The fabric (10) as claimed in claim 1 wherein each twisted inelastic yarn (50S, 50Z) has an S- or Z-twist of form 4 to 16 turns/cm (10 to 40 turns/inch).

6. The fabric (10) as claimed in claim 1 wherein the elasticised yarn (40*a*, 40*b*) has an elastically recoverable extension of from 50 to 120%.

7. The fabric (10) as claimed in claim 1 wherein the elasticised yarn (40*a*, 40*b*) comprises an elastomer, a heat set crimped yarn or a highly twisted inelastic yarn (50S, 50Z).

8. The fabric (10) as claimed in claim 7 wherein the elasticised yarn (40*a*, 40*b*) is made from polyurethane.

9. The fabric (10) as claimed in claim 8 wherein the yarn is a nylon wrapped polyurethane yarn.

10. A medical bandage manufactured from the fabric (10) as claimed in claim 1.

11. A bandage as claimed in claim 10 having a layer of a pressure sensitive adhesive over one surface thereof.

* * * * *